United States Patent [19]

Sumner, Jr. et al.

[11] Patent Number: 4,786,748

[45] Date of Patent: Nov. 22, 1988

[54] PROCESSES FOR PREPARING AKLYLENE AND DIALKYL KETALS AND ALKYL ALPHA-ENOL ETHERS OF ALPHA-ACETYL CINNAMIC ACIDS OR ESTERS THEREOF

[75] Inventors: Charles E. Sumner, Jr.; Joseph R. Zoeller, both of Kingsport, Tenn.

[73] Assignee: Eastman Kodak Company, Rochester, N.Y.

[21] Appl. No.: 107,744

[22] Filed: Oct. 13, 1987

[51] Int. Cl.[4] .............................................. C07C 69/76
[52] U.S. Cl. ..................... 560/60; 562/470; 562/426; 560/10
[58] Field of Search ................... 560/60, 10; 562/470, 562/426

[56] References Cited

PUBLICATIONS

Gasparrini et al, *Tetrahedron,* 40:1491 (1984).
Jones, *Org. Reactions,* 15:204 (1967).

*Primary Examiner*—Paul J. Killos
*Attorney, Agent, or Firm*—Charles R. Martin; William P. Heath, Jr.

[57] ABSTRACT

Alkylene or dialkyl ketal of an alpha-acetyl cinnamic acid or ester therof are obtained by reacting alpha-acetyl cinnamic acid or an ester thereof with a ketalizing agent selected from the group consisting of alkyl glycols, dialkyl detals and trialkyl orthoesters in the presence of the transition metal catalyst and an acid catalyst. Also, alkyl alpha-enol ethers of alpha-acetyl cinnamic acid are obtained by heating the alkylene or dialkyl ketals.

12 Claims, No Drawings

PROCESSES FOR PREPARING AKLYLENE AND DIALKYL KETALS AND ALKYL ALPHA-ENOL ETHERS OF ALPHA-ACETYL CINNAMIC ACIDS OR ESTERS THEREOF

BACKGROUND OF THE INVENTION

1. Field of the Invention

The present invention relates to a novel process for preparing alkylene or dialkyl ketals of alpha-acetyl cinnamic acids or esters thereof by reacting an alpha-acetyl cinnamic acid or ester thereof with a ketalizing agent in the presence of a transition metal catalyst and an acid catalyst. This invention also relates to a process for producing aliphatic alpha-enol ethers of alpha-acetyl cinnamic acids or esters thereof.

The ketals and alpha-enol ethers produced by the processes of the invention can be used directly to synthesize naphthanoic acids or esters thereof.

2. Description of the Background

Substituted ketals, alpha-enol ethers or alpha-enol esters of alpha-acetyl cinnamic acids or esters thereof are useful for the synthesis of substituted 2-naphthanoic acids and esters thereof which are polymer intermediates. In order for 2-naphthanoic acid derivatives to be useful polymer intermediates a second functional group besides the carboxyl group must be present on the aromatic ring. Moreover, such functional group must be present at a specific location on the molecule. Consequently, it is important tht the alkylene and dialkyl ketones and alkyl alpha-enol ethers of alpha-acetyl cinnamic acids or esters thereof from which the 2-naphthanoic acid derivatives are obtained be substituted at specific sites on the aromatic ring. The development of such a process is of great significance to the industry.

A number of general methods for the ketalization of ketones are known (Gasparrini, F., Giovannoli, M., and Misiti, D., Tetrahedron 40: 1491 (1984) and references cited therein). These methods include the synthesis of ethylene and dimethyl ketals from alpha-beta unsaturated ketones. These methods, however, utilize no transition metal catalysts. Moreover, no known applications of these methods to alpha-acetyl cinnamic acids or esters thereof are known.

Accordingly, there is still a need for a general process for the synthesis in good yield of alkylene and dialkyl ketals and alpha-enol ethers of alpha-acetyl cinnamic acids and esters thereof having a predictable substitution pattern and good yield.

SUMMARY OF THE INVENTION

This invention relates to a process for preparing an alkylene or dialkyl ketal of the formula

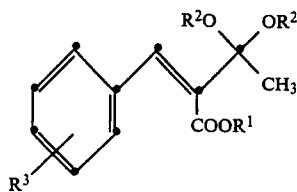

wherein $R^1$ is H, $(C_1-C_{12})$alkyl, $(C_6-C_{20})$aryl or $(C_7-C_{21})$aralkyl or alkylaryl, each $R^2$ is $(C_1-C_{12})$alkyl or two $R^2$ together are $(C_2-C_{12})$alkylene, and $R^3$ is H, halo, carboxy or $(C_1-C_{12})$alkyl, alkoxy, acyl, acyloxy, carbalkoxy or alkylthio, said process comprising reacting an alpha-acetyl cinnamic acid or ester thereof of the formula

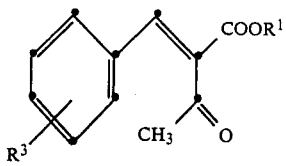

wherein $R^1$ and $R^3$ are as defined above, with a ketalizing agent selected from the group consisting of alkyl glycols, dialkyl ketals and trialkyl orthoesters, in the presence of a transition metal catalyst and an acid catalyst; said cinnamic acid or ester thereof and said ketalizing agent being present in a proportion and under reaction conditions effective to produce said ketal.

This invention also relates to a process for producing an alkylene or dialkyl ketal of the formula

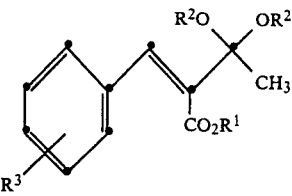

wherein $R^1$ is $H_1(C_1-C_{12})$alkyl, $(C_6-C_{20})$aryl or $(C_7-C_{21})$aralkyl or alkylaryl, each $R^2$ is $(C_1-C_{12})$alkyl or two $R^2$ together are $(C_2-C_{12})$alkylene, and $R^3$ is H, halo, carboxy or $(C_1-C_{12})$alkyl, alkoxy, acyl, acyloxy, carbalkoxy or alkylthio, said process comprising, reacting a compound selected from the group consisting acetoacetic acid or an ester thereof of the formula

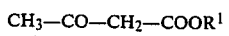

$$CH_3-CO-CH_2-COOR^1$$

wherein $R^1$ is as defined above, with a benzaldehyde of the formula

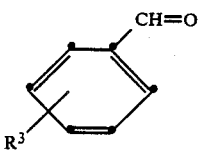

wherein $R^3$ is as defined above; said compound and said benzaldehyde being present in a proportion and under reaction conditions effective to form an alpha-acetyl cinnamic acid or ester thereof of the formula

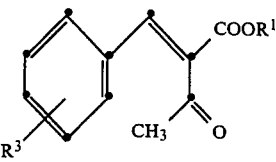

wherein $R^1$ and $R^3$ are as defined above, and reacting said alpha-acetyl cinnamic acid or ester thereof with a ketalizing agent selected from the group consisting of alkyl glycols, dialkyl ketals and trialkyl orthoesters, in the presence of a transition metal catalyst and an acid catalyst; said cinnamic acid or ester thereof and said ketalizing agent being present in a proportion and under reaction conditions effective to form said alkylene or dialkyl ketal.

This invention also relates to a process for producing an alkyl alpha-enol ether of the formula

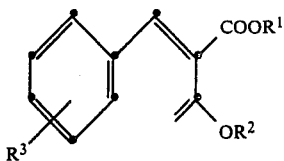

wherein $R^1$ is H, $(C_1-C_{12})$alkyl, $(C_6-C_{20})$aryl or $(C_7-C_{21})$aralkyl or alkylaryl, $R^2$ is $(C_1-C_{12})$alkyl, and $R^3$ is H, halo, carboxy, or $(C_1-C_{12})$alkyl, alkoxy, acyl, acyloxy, carbalkoxy or alkylthio, said process comprising heating an alkylene or dialkyl at a temperature sufficient to form said alpha-enol ether.

In addition, this invention also relates to a process for producing an alkyl alpha-enol ether of the formula

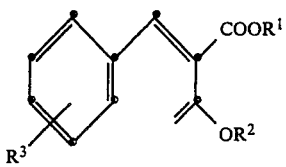

wherein $R^1$ is H, $(C_1-C_{12})$alkyl, $(C_6-C_{20})$aryl or $(C_7-C_{21})$aralkyl or alkylaryl, $R^2$ is $(C_1-C_{12})$alkyl, alkoxy, acyl, acyloxy, carbalkoxy or alkylthio, said process comprising reacting a compound selected from the group consisting of acetoacetic acid or an ester thereof of the formula $$CH_3-CO-CH_2-COOR^1$$

wherein $R^1$ is as defined above and acetylacetone with a benzaldehyde of the formula

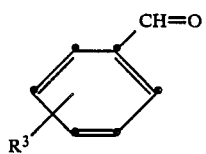

wherein $R^3$ is as defined above; said compound and said benzaldehyde being present in a proportion and under reaction conditions effective to form an alpha-acetyl cinnamic acid or ester thereof of the formula

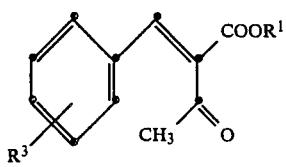

wherein $R^1$ and $R^3$ are as defined above;
reacting said alpha-acetyl cinnamic acid or ester thereof with a ketalizing agent selected from the group consisting of alkyl glycols, dialkyl ketals, and trialkyl orthoesters, in the presence of a transition metal catalyst and an acid catalyst; said cinnamic acid or ester thereof and said ketalizing agent being present in a proportion and under reaction conditions effective to form said alkylene or dialkyl ketal; and heating said ketal at a temperature sufficient to form said alpha-enol ether.

A more complete appreciation of the invention and many of the attendant advantages thereof will be readily perceived as the same becomes better understood by reference to the following detailed description of the preferred embodiment thereof.

DESCRIPTION OF THE PREFERRED EMBODIMENTS

The ketalization of ketones by exchange with preformed ketals such as the dimethyl ketal of acetone or trialkyl orthoesters described by the prior art are workable processes for the synthesis of simple chemical structures. However, the ketalization of alpha-beta unsaturated ketones having a tertiary double bond presents severe restrictions for the ketalization reaction. Under most circumstances, this reaction does not go to completion and when a product is formed, it is formed in extremely low yields.

The present invention revolves around the finding that the addition of a catalytic amount of a transition metal catalyst to the reaction mixture containing an alpha-acetyl cinnamic acid or ester thereof, an acid catalyst and a ketalizing agent is unexpectedly beneficial to the reaction in that the reaction proceeds favorably and provides alkylene or dialkyl ketene product in in high yields.

In the absence of the transition metal catalyst the reaction gradually slows down and virtually stops at about 70% completion. The introduction of a transition metal catalyst into the reaction mixture brings about the unexpected result that the ketalization reaction goes to greater than about 95% completion in a very short period of time.

Suitable ketalizing agents for use in the process of the invention are alkyl glycols, dialkyl ketals, dialkyl acetals and trialkyl orthoesters such as 1,2- and 1,3- $(C_2-C_{12})$glycols, $(C_1-C_{12})$trialkyl orthoesters derived from $C_1-C_{12}$ acids, and $(C_1-C_{12})$dialkyl ketals derived from $(C_1-C_{12})$ketones. Examples of suitable glycols and orthoformates are neopentyl glycol, propanediol, 1,2- and 1,3-ethylene glycol, tri-methyl orthoformate and the like. Preferred are alkyl glycols and alkyl orthoformates having 1–12 carbon atoms. Alkyl glycols, dialkyl ketals, and tri-alkyl orthoformates are commercially available or may be prepared by methods known in the art.

The alpha-acetyl cinnamic acid or ester thereof may be substituted with halo such as chloro or bromo, carboxyl or lower alkyl, alkoxy, acyl, acyloxy, carbalkoxy or alkylthio. Preferred are methyl, ethyl, isopropyl, tertbutyl, methoxy, ethoxy, acetoxy, acetyl, methylthio and ethylthio. The aromatic ring may be substituted at the ortho, meta or para positions of the aromatic ring with respect to the carboxyl containing substituent. Preferred are substituents located at the ortho and para positions, and more preferrably at the para position.

The acid catalyst used in the process of the invention can be any of the acid catalysts conventionally utilized in the ketalization of ketones and include strong acids such as sulfuric acid, trifluoroacetic acid, hydrochloric acid or sulfonic acid, and acid resins such as acid-exchange resins. Acidic resins are commercially available or can be prepared by methods known in the art. A preferred acid resin for the present invention is Amberlyst 15 ®. The concentration of acid catalyst employed will vary but will always be used in catalytic amounts that generally fall in the range of 0.01 to 0.1 equivalents/mole of α-acetyl cinnamate.

The transition metal catalyst for the ketalization reaction of the invention can be any transition metal olefin isomerization catalyst which isomerizes the unreacted isomer of the ketone reactant into a more reactive isomer and thereby provide a constant supply of reactive ketone. Preferred isomerization catalysts are Group VIII metal catalysts, e.g., rhodium, ruthenium cobalt and palladium catalysts and derivatives thereof such as cobalt hydrides, and palladium hydrides among others. Particularly preferred among the transition metal catalysts are carbonylhydride tris(triphenylphosphine)rhodium and hydridochlorocarbonyl tris(triphenylphosphine)ruthenium. The transition metal catalyst will always be used in catalytic amounts which usually fall in the range of 0.01 to 0.0001 mole/mole of α-acetyl cinnamate. The proportion of the acid catalyst to transition metal catalyst generally ranges from about 10:1 to 10,000:1, and more preferably 50:1 to 5,000:1 by weight.

In the reaction of the substituted alpha-acetyl cinnamic acid or ester thereof to ketalizing agent may vary widely but ordinarily fall in the range of about 1:1 to 1:5 molar equivalents, preferably about 1:1 to 1:3 molar equivalents. The reaction temperatures employed are those sufficient to effect the ketalization reaction and normally fall in the range of about 25° to 250° C., preferably about 40° to 200° C. The reaction proceeds readily at atmospheric pressure but the reaction can be conducted under pressure if desired.

The ketalization reaction may be conducted in a liquid phase and an inert solvent may be added. Within the context of this invention, an inert solvent is defined as a solvent which does not alter the composition of either the reactants, solvents, or catalysts. Examples of inert solvents are acyclic, cyclic, and aromatic hydrocarbons, halides thereof or their axeotropes formed with water, alcohols, and glycols from which the alkylene and alkyl residues of the R² substituents of the ketals are derived. A preferred group of solvents are alcohols or glycols such as methanol, ethanol, and ethylene glycol.

Alpha-acetyl cinnamic acid or ester thereof may be obtained by reacting a compound such as acetoacetic acid or an ester thereof of the formula $CH_3-CO-CH_2COOR^1$ wherein $R^1$ is as defined above or acetylacetone with a benzaldehyde substituted with $R^3$, wherein $R^3$ is as defined above. The Knoevenagel condensation of aromatic aldehydes and acetoacetic esters is a well known and efficient process for generating alpha-acetyl cinnamic acid esters (Jones, Org. Reactions 15: 204 (1967), the content of which is incorporated herein by reference). The reaction of acetoacetone with a substituted aromatic benzaldehyde can also be conducted under conditions similar to those of the Knoevenagel reaction.

In general, the reaction of acetoacetic acid or an ester thereof or the acetylacetone with the benzaldehyde is conducted at a temperature of about 0° to 250° C., and more preferably about 50° to 150° C., and at a pressure of about 0.1 mmHg to 10 atm, preferably about 1 atm. In this reaction, the acetoacetic acid or ester thereof and the benzaldehyde are preferably present in a proportion of about 25:1 to 1:25, and more preferably about 1:1 to 1;2 by weight.

In a further aspect of the invention, a process is provided for producing alkyl alpha-enol ethers of the formula

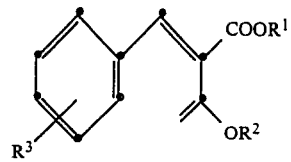

wherein $R^1$ and $R^3$ are as defined above and $R^2$ is $(C_1-C_{12})$alkyl, by heating the alkylene or dialkyl ketals of the invention describe below, preferably at about 25° to 300° C., preferably at about 75° to 275° C., more preferably about 125° to 175° C. Alternatively, the alkyl alpha-enol ether can be obtained by simply distilling the alkylene.

Suitable $R^1$ groups in the structures of the compounds illustrated and discussed above include H; alkyl groups such as methyl, ethyl, propyl, butyl, pentyl, hexyl, decyl, and the like; aryl groups such as phenyl, naphthyl and the like; alkyaryl such as tolyl, anthryl and the like; aralkyl such as benzyl, phenylethyl, phenylpropyl, phenylbutyl and the like.

Illustrative of suitable $R^2$ groups in the structures are methyl, ethyl, propyl, butyl, pentyl, hexyl, decyl and the like and examples of suitable $R^2$ groups in the ketal when taken together are ethylene, trimethylene, tetramethylene and the like.

Exemplary of $R^3$ groups are hydrogen, halo such as chloro, bromo and fluoro; carboxy; alkyl such as described for $R^1$ and $R^2$; alkoxy such as methoxy, ethoxy, propoxy, butoxy, pentoxy and the like; acyl such as ethanoyl, propanoyl, butanoyl, pentanoyl an the like; acyloxy such as ethanoyloxy, propanoyloxy, butanoyloxy, pentanoyloxy and the like; carbalkoxy such as methoxycarbonyl, ethyoxycarbonyl, propoxycarbonyl, butoxycarbonyl, etc.; alkylthio such as methylthio, ethylthio, propylthio, butylthio, pentylthio, etc.

The products obtained by practicing the processes of the invention may be separated from the reaction mixtures by methods known in the art, such as distillation and the like.

The processes of this invention provide a simple and inexpensive means for obtaining the alkylene and dialkyl ketals and alkyl alpha-enol ethers of alpha-acetyl cinnamic acids or esters thereof in high yields. Typical yields of the alkylene and dialkyl ketals obtained by the process of the invention are greater than about 95% and can be attained in periods of time of less than about 6 hours in many cases. Similar yields of the alpha-enol ethers of alpha-acetyl cinnamic acids or esters thereof are obtained.

Having now generally described this invention, the same will be better understood by reference to certain specific examples, which are included herein for purposes of illustration only and are not intended to be limiting of the invention or any embodiments thereof, unless so specified.

EXAMPLE 1

Preparation of Ethylene Ketal of Methyl-p-methyl α-Acetyl Cinnamate in the Presence of Rhodium Catalyst To a 500-mL, three-neck flask equipped with a Dean-Stark trap are added methyl-p-methyl α-acetyl cinnamate (51 g; 0.234 mol), ethylene glycol (50 g; 0.806 mol), carbonylhydrido tris(triphenylphosphine)rhodium (0.250 g; 0.27 mmol), an acidic resin, e.g., Amberlyst-15 ® (1.00 g) and cyclohexane (150 mL). The mixture is heated at reflux for 5.5 hours while water produced by the reaction is collected. When 20 mL of the ethylene glycol/water layer are collected in a Dean-Stark trap, the layer is removed from the trap and an additional 20 mL of dry ethylene glycol are added to the reaction mixture. The mixture is sampled periodically and analyzed by GC and (H)NMR. The initial ratio of the two isomers of the ketone (the Z isomer to the E isomer) is 1.3:1.0. This ratio remains essentially constant throughout the reaction. After 5 hours the ketone is about 90% converted in the ethylene ketal. Of the unconverted ketone, the ratio of Z to E isomers as determined from the (H)NMR spectrum is still about 1.3:1.

This example illustrates that a transition metal catalyst is required for the reaction to proceed with a high yield.

EXAMPLE 2

Preparation of Ethylene Ketal of Methyl-p-Methyl α-Acetyl Cinnamate in the Absence of a Transition Metal Catalyst This example demonstrates the necessity of the transition metal isomerization catalyst in generating high conversions to and high yields of the ketal.

The procedure described in Example 1 is followed except that the rhodium catalyst is left out. After 5.5 hours, the ketone is only 71% converted to the ethylene ketal. Of the unconverted ketone the ratio of the Z to the E isomers is about 0.3:1.0. It can be seen from the (H)NMR spectrum of samples taken during the reaction that the Z isomer is preferentially converted to the ketal.

EXAMPLE 3

Preparation of Ethylene Ketal of Methyl-p-Methyl α-Acetyl Cinnamate in the Presence of Rhodium Catalyst The procedure outlined in Example 1 is followed except that the cyclohexane solvent is replaced with toluene. After 5 hours, the ketone is 95% converted to the ethylene ketal.

EXAMPLE 4

Preparation of Ethylene Ketal of Methyl-p-Methyl α-Acetyl Cinnamate in the Absence of a Transition Metal Catalyst This example illustrates that a transition metal catalyst is required for the ketalization reaction to proceed with a high yield.

The procedure outlined in Example 1 is followed except that toluene is used in place of cyclohexane and the rhodium catalyst is left out. After 5.5 hours, the ketone is only about 70% converted to the ethylene ketal.

EXAMPLE 5

Preparation of Ethylene Ketal of Methyl-p-Methyl α-Acetyl Cinnamate in the Presence of Ruthenium Catalyst The procedure outlined in Example 1 is followed except that toluene is used in place of cyclohexane and hydridochlorocarbonyl tris(triphenylphosphine)rhodium. After 5.5 hours, about 95% of the ketone has been converted to the ethylene ketal as is also the case with the rhodium catalyst.

EXAMPLE 6

Comparative Preparation of Dimethyl Ketal of Methyl-p-Methyl-Alpha-Acetyl Cinnamate With and Without Rhodium Catalyst This example demonstrates the utility of this process in generating dialkyl ketals by ketal exchange. A solution of methyl-p-methyl-alpha-acetyl cinnamate (5.45 grams, 0.025 moles) in 30 mL of 1/1 (v/v) trimethyl orthoformate/methanol is added to a 50-mL, round-bottom flask containing 0.60 grams of an acidic resin, e.g., Amberlyst-15 ® resin, and 10 mg of carbonylhydrido tris(triphenylphosphine)rhodium (process of the invention). This solution is stirred magnetically at room temperature and samples removed periodically.

A separate reaction is run under the same conditions except that the rhodium catalyst is omitted (prior art process).

Based on the NMR spectra of samples removed during the course of the reaction conducted in the absence of the rhodium catalyst (prior art process), the Z isomer of the ketone is rapidly depleted (4.75 hours) while the E isomer is still present. In the reaction conducted in the presence of the rhodium catalyst (process of the invention), both isomers are always in evidence until the reaction is <98% complete.

The reaction conducted in the presence of the catalyst (present invention) is >98% complete in 6 hours whereas the reaction conducted in the absence of the catalyst (prior art) is only 82% complete over the same time period. Allowing the reaction without catalyst (prior art) to continue for longer periods of times does not increase the rate or extent of conversion of substrate to product. The reaction conducted in th absence of the catalyst prior art is only 85% complete in 30 hours.

The ketal product of the reaction conducted with the catalyst (present invention) can be recovered in >95% yield after sequentially filtering the reaction mixture, neutralizing any acidity remaining wth a slightly basic resin, e.g., Amberlyst-21 ®, filtering again, and then removing the solvent in vacuo.

The invention now being fully described, it will be apparent to one of ordinary skill in the art that many changes and modification can be made thereto without departing from the spirit or scope of the invention as set forth herein.

What is claimed is:

1. A process for preparing an alkylene or dialkyl ketal of the formula

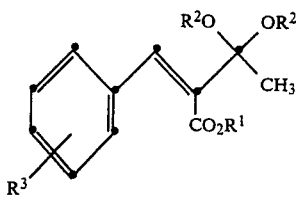

wherein $R^1$ is H, $(C_1-C_{12})$alkyl, $(C_6-C_{20})$aryl or $(C_7-C_{21})$aralkyl or alkylaryl, each $R^2$ is $(C_1-C_{12})$alkyl or two $R^2$ together are $(C_2-C_{12})$alkylene, and $R^3$ is H, halo, carboxy or $(C_1-C_{12})$alkyl, alkoxy, acyl, acyloxy, carbalkoxy or alkylthio, said process comprising reacting an alpha-acetyl cinnamic acid or ester thereof of the formula

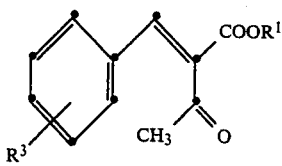

wherein $R^1$ and $R^3$ are as defined above, with a ketalizing agent selected from the group consisting of alkyl glycols, dialkyl ketals, dialkyl acetals, and trialkyl orthoesters, in the presence of a transition metal catalyst and an acid catalyst; said cinnamic acid or ester thereof and said ketalizing agent being present in a proportion and under reaction conditions effective to produce said ketal.

2. The process of claim 1, wherein the acid catalyst is a strong acid selected from the group consisting of sulfuric acid, sulfonic acid, trifluoroacetic acid an hydrofluoric acid.

3. The process of claim 1, wherein the acid is an acidic resin.

4. The process of claim 1, wherein the transition metal catalyst is selected from the group consisting of rhodium, ruthenium, cobalt and palladium catalysts.

5. The process of claim 4, wherein the transition metal catalyst is selected from the group consisting of carbonylhydride tris(triphenylphosphine)rhodium and hydridochlorocarbonyl tris(triphenylphosphine)ruthenium.

6. The process of claim 1, wherein the ketalizing agent is a $(C_1-C_{12})$trialkyl orthoformate.

7. The process of claim 1, wherein the acid and the catalyst are present in a proportion of about 10:1 to 10,000:1 by weight.

8. The process of claim 1, wherein the proportion of the cinnamic acid or ester thereof to the ketalizing agent is about 1:1 to 1:5 molar equivalents.

9. The process of claim 1, wherein the cinnamic acid or ester thereof and the ketalizing agent are reacted at a temperature of about 25° to 250° C.

10. A process for producing an alkylene or dialkyl ketal of the formula

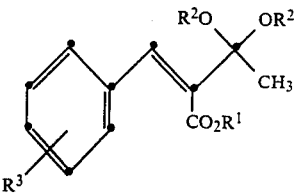

wherein $R^1$ is H, $(C_1-C_{12})$alkyl, $(C_6-C_{20})$aryl or $(C_7-C_{21})$aralkyl or alkylaryl, $R^2$ is $(C_1-C_{12})$alkyl and $R^3$ is H, halo, carboxy or $(C_1-C_{12})$alkyl, alkoxy, acyl, acyloxy, carbalkoxy or alkylthio, said process comprising reacting a compound selected from the group consisting of acetoacetic acid or an ester thereof of the formula

$$CH_3-CO-CH_2-COOR^1$$

wherein $R^1$ is as defined above, and acetylacetone with a benzaldehyde of the formula wherein $R^3$ is as defined above, said compound and said benzaldehyde being present in a proportion and under conditions effective to form an alpha-acetyl cinnamic acid or ester thereof of the formula

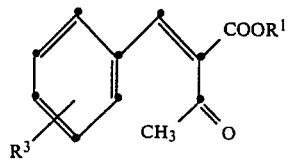

wherein $R^1$ and $R^3$ are as defined above; and reacting said alpha-acetyl cinnamic acid or ester thereof with a ketalizing agent selected from the group consisting of alkyl glycols, dialkyl ketals, dialkyl acetals, and trialkyl orthoesters in the presence of a transition metal catalyst and an acid; said cinnamic acid or ester thereof and said ketalizing agent being present in a proportion and under conditions effective to form an alkyl ketal of the alpha-acetyl cinnamic acid or ester thereof.

11. The process of claim 10, wherein the acid is a strong acid selected from the group consisting of sulfuric acid, sulfonic acid, trifluoroacetic acid and hydrofluoric acid.

12. The process of claim 10, wherein the acid is an acid resin.

13. The process of claim 10, wherein the transition metal catalyst is selected from the group consisting of rhodium, ruthenium, cobalt and palladium catalysts.

14. The process of claim 4, wherein the transition metal catalyst is selected from the group consisting of carbonylhydride tris(triphenylphosphine)rhodium and hydridochlorocarbonyl tris(triphenylphosphine)ruthenium.

15. The process of claim 10, wherein the acid and the catalyst are present in a proportion of about 10:1 to 10,000:1 by weight.

16. The process of claim 13, wherein the proportion of the cinnamic acid or ester thereof to the ketalizing agent is about 1:1 to 1:5 molar equivalents.

17. The process of claim 10, wherein the cinnamic acid or ester thereof and the ketalizing agent are reated at a temperature of about 25° to 250° C.

18. A process for producing an alkyl alpha-enol ether of the formula

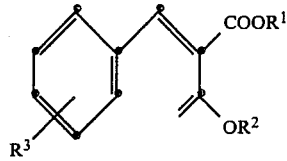

wherein $R^2$ is $(C_7-C_{21})$aralkyl or alkylaryl, $R^2$ is $(C_1-C_{12})$alkyl and $R^3$ is H, halo, carboxy or $(C_1-C_{12})$alkyl, alkoxy, acyl, acyloxy, carbalkoxy or alkylthio, said process comprising reacting a compound selected form the group consisting of acetoacetic acid or an ester thereof of the formula

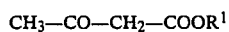

wherein $R^1$ is as defined above, and acetylacetone, with a benzaldehyde of the formula

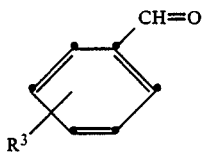

wherein $R^3$ is as defined above; said compound and said benzaldehyde being present in a proportion and under conditions effective to form an alpha-acetyl cinnamic acid or ester thereof of the formula

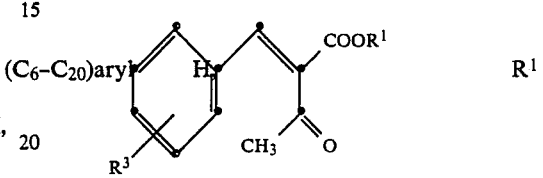

wherein $R^1$ and $R^3$ are as defined above;
reacting said alpha-acetyl cinnamic acid or ester thereof with a ketalizing agent selected from the group consisting of alkyl glycols, dialkyl ketals, dialkyl acetals, and trialkyl orthoesters in the presence of a transition metal catalyst and an acid; said cinnamic acid or ester thereof and said ketalizing agent being present in a proportion and under conditions effective to form an alkylene or dialkyl ketal of said alpha-acetyl cinnamic acid or ester thereof; and
heating said ketal at a temperature of about 25° to 300° C. to form an alkyl alpha-enol ether of said alpha-acetyl cinnamic acid or ester thereof.

* * * * *